United States Patent
Milway et al.

(10) Patent No.: US 12,262,720 B2
(45) Date of Patent: Apr. 1, 2025

(54) ALGAL OIL WITH IMPROVED NUTRITIONAL VALUE

(71) Applicant: MARA RENEWABLES CORPORATION, Dartmouth (CA)

(72) Inventors: Michael Milway, Dartmouth (CA); Laura Purdue, Dartmouth (CA); Zachary Sun, Dartmouth (CA); Mercia Valentine, Dartmouth (CA); Joshua Lowrey, Dartmouth (CA); Roberto E. Armenta, Dartmouth (CA)

(73) Assignee: Mara Renewables Corporation, Dartmouth (CA)

( * ) Notice: Subject to any disclaimer, the term of this patent is extended or adjusted under 35 U.S.C. 154(b) by 902 days.

(21) Appl. No.: 17/289,177

(22) PCT Filed: Nov. 1, 2019

(86) PCT No.: PCT/IB2019/059390
§ 371 (c)(1),
(2) Date: Apr. 27, 2021

(87) PCT Pub. No.: WO2020/089845
PCT Pub. Date: May 7, 2020

(65) Prior Publication Data
US 2021/0392913 A1    Dec. 23, 2021

Related U.S. Application Data

(60) Provisional application No. 62/754,896, filed on Nov. 2, 2018.

(51) Int. Cl.
*A23D 9/02* (2006.01)
*C12P 7/6472* (2022.01)
*C12R 1/89* (2006.01)

(52) U.S. Cl.
CPC .............. *A23D 9/02* (2013.01); *C12P 7/6472* (2013.01); *C12R 2001/89* (2021.05)

(58) Field of Classification Search
CPC . A23D 9/02; A23D 9/00; C12P 7/6472; C12P 7/64; C12R 2001/89; A01G 33/00;
(Continued)

(56) References Cited

U.S. PATENT DOCUMENTS 7,381,558 B2    6/2008   Barclay
8,163,515 B2    4/2012   Burja et al.
(Continued)

FOREIGN PATENT DOCUMENTS

CN    106795539 A     5/2017
EP     2960325 A1    12/2015
(Continued)

OTHER PUBLICATIONS

Singh, et al. ("Docosahexaenoic acid (DHA) production by *Thraustochytrium* sp. ATCC 20892." World Journal of Microbiology and Biotechnology 12 (1996): 76-81). (Year: 1996).*
(Continued)

*Primary Examiner* — Terry A McKelvey
*Assistant Examiner* — Andrew T Moehlman
(74) *Attorney, Agent, or Firm* — Kilpatrick Townsend & Stockton LLP

(57) ABSTRACT

Provided herein are fermentation methods that improve the nutritional value and physical properties of microbial oil. Specifically, provided is a method of producing oil with increased omega-7 fatty acids. The method comprises culturing oil-producing microorganisms in a fermentation medium with less than 0.3 mg/L zinc, wherein the culturing produces an oil comprising fatty acids, wherein the oil
(Continued)

comprises increased omega-7 fatty acids compared to a control oil. Optionally, the oil is isolated from the microorganisms of the culture.

37 Claims, 5 Drawing Sheets

(58) Field of Classification Search
 CPC ....... A23K 20/158; A23L 33/115; C11B 1/00; A61K 8/36; A61K 31/202; C12N 1/12
 See application file for complete search history.

(56) References Cited

U.S. PATENT DOCUMENTS

| | | | |
|---|---|---|---|
| 8,313,911 B2* | 11/2012 | Jackson | C12P 7/6434 435/6.15 |
| 9,023,616 B2* | 5/2015 | Radianingtyas | A61P 39/06 435/41 |
| 10,188,596 B2 | 1/2019 | Liu et al. | |
| 11,198,891 B2 | 12/2021 | Ugalde et al. | |
| 11,413,263 B2 | 8/2022 | Hadley et al. | |
| 11,466,297 B2 | 10/2022 | Sun et al. | |
| 2009/0117194 A1 | 5/2009 | Burja et al. | |
| 2012/0244584 A1 | 9/2012 | Zhang et al. | |
| 2013/0129775 A1* | 5/2013 | Shinde | A23K 20/158 424/195.17 |
| 2015/0176042 A1 | 6/2015 | Dennis et al. | |
| 2017/0356018 A1* | 12/2017 | Sun | C12P 7/6434 |
| 2018/0042839 A1* | 2/2018 | Liu | C11B 3/16 |
| 2018/0208954 A1 | 7/2018 | Sun et al. | |

FOREIGN PATENT DOCUMENTS

| | | |
|---|---|---|
| JP | 06253872 A | 9/1994 |
| JP | 2013507454 A | 3/2013 |
| JP | 2018520636 A | 8/2018 |
| WO | 2007069078 A2 | 6/2007 |
| WO | 2017212322 A1 | 12/2017 |

OTHER PUBLICATIONS

JP2021-519825, "Office Action", Sep. 26, 2023, 14 pages.
JP2021-519825, "Office Action", Jan. 23, 2024, 4 pages.
CA3,117,844, "Office Action", Oct. 30, 2023, 5 pages.
Bernstein et al., "Purified Palmitoleic Acid for the Reduction of High-Sensitivity C-Reactive Pprotein and Serum Lipids: A Double-Blinded, Randomized, Placebo Controlled Study", Journal of Clinical Lipidology, vol. 8, No. 6, 2014, pp. 612-617.
De Souza , "Is Palmitoleic Acid a Plausible Nonpharmacological Strategy to Prevent or Control Chronic Metabolic and Inflammatory Disorders?", Molecular Nutrition & Food Research, vol. 62, No. 1700504, 2018, 12 pages.
Dou et al., "The Effects of Trace Elements on the Lipid Productivity and Fatty Acid Composition of Nannochloropis Oculata", Journal of Renewable Energy, vol. 2013, Available Online at: https://downloads.hindawi.com/journals/jre/2013/671545.pdf, Jan. 1, 2013, pp. 1-6.
EP19879854.8 , "Extended European Search Report", Jul. 12, 2022, 10 pages.
Field et al., "Human Health Benefits of Vaccenic Acid", Applied Physiology Nutrition and Metabolism, vol. 34, No. 5, Oct. 2009, pp. 979-991.
Nagano et al., "Effect of Trace Elements on Growth of Marine Eukaryotes, Tharaustochytrids", Journal of Bioscience and Bioengineering, vol. 116, No. 3, Sep. 2013, pp. 337-339.
PCT/IB2019/059390 , "International Preliminary Report on Patentability", May 14, 2021, 7 pages.
PCT/IB2019/059390 , "International Search Report and Written Opinion", Jan. 3, 2020, 9 pages.
Ren et al., "Compositional Shift in Lipid Fractions During Lipid Accumulation and Turnover in *Schizochytrium* Sp", Bioresource Technology, vol. 157, Apr. 1, 2014, pp. 107-113.
Swanson et al., "Omega-3 Fatty Acids EPA and DHA: Health Benefits Throughout Life", Advances in Nutrition, vol. 3, No. 1, Jan. 2012, 7 pages.
Yang et al., "Chronic Administration of Palmitoleic Acid Reduces Insulin Resistance and Hepatic Lipid Accumulation in KK-Ay Mice with Genetic Type 2 Diabetes", Lipids in Health and Disease, vol. 10, No. 120, Jul. 21, 2011, pp. 1-8.
Yang et al., "Fatty Acid Composition of Lipids in Sea Buckthorn (*Hippophae rhamnoides* L.) Berries of Different Origins", Journal of Agricultural and Food Chemistry, vol. 49, No. 4, Apr. 2001, pp. 1939-1947.
CN201980069686.0, "Office Action" with machine translation, Aug. 14, 2024, 11 pages.
Ye et al., "Research Progress in DHA Production by Thraustochytrids", Chemical Industry and Engineering Progress, vol. 39, No. 8, 2020, pp. 3235-3245.
CN201980069686.0, "Office Action", Feb. 29, 2024, 14 pages.

* cited by examiner

ALGAL OIL WITH IMPROVED NUTRITIONAL VALUE

CROSS-REFERENCE TO RELATED APPLICATIONS

This application claims priority to U.S. Provisional Application No. 62/754,896, filed Nov. 2, 2018, which is incorporated by reference herein in its entirety.

BACKGROUND

Omega-7 fatty acids, mainly palmitoleic acid (C16:1 n-7) and vaccenic acid (C18:1 n-7), belong to the group designated monounsaturated fatty acids (MUFA). In recent years, studies on the nutritional value of omega-7 fatty acids have indicated potential health benefits of palmitoleic acid (C16:1 n-7) and vaccenic acid (C18:1 n-7) (Field et al. 2009 Appl. Physiol. Nutr. Metab. 34:979-91; Yang et al. 2011 Lipids in Health and Disease 10:120; Bernstein et al. 2014 Journal of Clinical Lipidology 8:612-17; Souza et al. 2018 Mol. Nutr. Food Res. 61:1700504). Currently, products rich in omega-7 fatty acids are typically obtained from plant sources, such as sea buckthorn (*Hippophae rhamnoids*) and macadamia nut oil (*Macadamia integrifolia*), as well as animal sources such as mink oil (Yang et al. 2001 J. Agric. Food Chem. 49:1939-47; Souza et al. 2018 Mol. Nutr. Food Res. 61:1700504). However, these sources are in limited supply so omega-7 fatty acids are only used as premium ingredients for food supplements and cosmetics.

BRIEF SUMMARY

Provided herein are fermentation methods that improve the nutritional value and physical properties of microbial oil. Specifically, provided is a method of producing oil with increased omega-7 fatty acids. The method comprises culturing oil-producing microorganisms in a fermentation medium with less than 0.3 mg/L zinc, wherein the culturing produces an oil comprising fatty acids, wherein the oil comprises increased omega-7 fatty acids compared to a control oil. Optionally, the oil is isolated from the microorganisms of the culture. Optionally, 35% or less of the fatty acids of the oil are saturated fatty acids.

DETAILED DESCRIPTION

Figure 1:
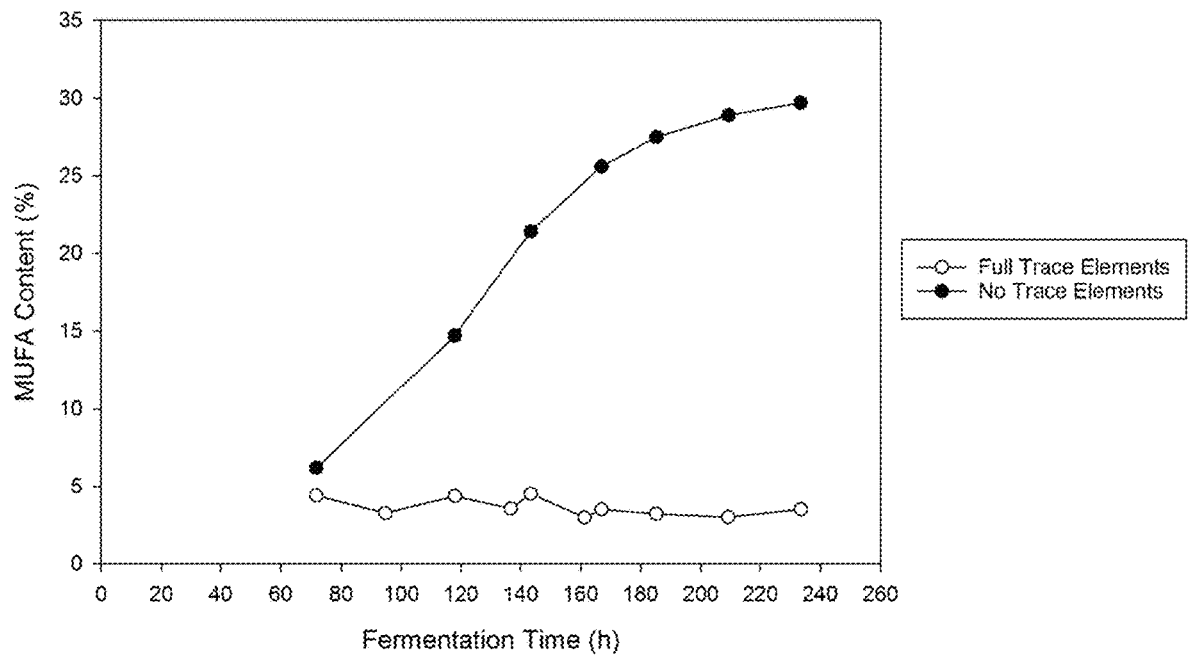
FIG. 1 is a graph showing monounsaturated fatty acid concentration produced by thraustochytrid culture with (empty circle) and without (filled circle) trace element addition over the course of a fed batch fermentation.

Efforts to produce omega-7 fatty acids using photosynthetic algae such as *Nannochloropsis* (U.S. Publication No. 2013/0129775) have been problematic for 2 reasons. First, photosynthetic algae have low productivity and are, thus, not a commercially viable option for heterotrophic processes. Second, algae oil from photosynthetic algae like *Nannochloropsis* contain negligible amounts of DHA, which has unique benefits in brain and retina development of infants and cognitive function of aging adults (Swanson et al., 2012 Adv. Nutr. 3:107). Algal oil produced by heterotrophic marine microalgae (U.S. Pat. No. 7,381,558) mainly contains long chain polyunsaturated fatty acids (LC-PUFAs) such as DHA, EPA, and DPA and minimal amounts of omega-7 fatty acids. Although it is challenging to customize the fatty acid profile of algal oil to promote desired nutritional and physical properties without genetic modification of the algae, the present application provides an algal oil with both omega-3 and omega-7 fatty acids without genetic modification.

Using the fermentation process described herein, microorganisms produce oil with significantly better nutritional health benefits than the same microorganisms in different conditions. These improvements offer competitive advantages over typical algal oils in the market. The microbial fermentation process provided herein produces oils rich in omega-3 fatty acids (e.g., C22:6 (n-3) DHA), omega-6 fatty acids (e.g., C22:5 (n-6) DPA), and omega-7 fatty acids (e.g., C16:1 (n-7) palmitoleic acid and C18:1 (n-7) vaccenic acid). The oils are also low in saturated fatty acids (e.g., C16:0 palmitic acid and C14:0 myristic acid). Such fatty acid profiles are consistent with DHA-rich or omega-3 rich nutritional oils and have improved nutritional composition and value than oils low in omega-7 fatty acids. The provided methods include changing zinc concentrations in the culture media. The provided methods advantageously require no extra equipment, ingredients or process controls.

By applying the process conditions described herein, including controlling the level of zinc in the culture medium, the microorganisms produce oils with significantly increased amounts of polyunsaturated fatty acids (PUFA) and monounsaturated fatty acids (MUFA) and reduced saturated fatty acids (SFA) as compared to oils produced by other fermentation methods. The zinc content is reduced to less than 0.3 ng/ml in the culture medium. The zinc content includes the amount of zinc added to the culture medium and the residual amounts of zinc present in the water used for fermentation. The oils contains an improved nutritional value due to the increased PUFA (DHA and DPA) and MUFA (omega-7 fatty acids) amounts in the total fatty acids as compared to control oils.

Cold flow properties ease handling and processing of extracted oils. Initial oil content may include, for example, a high proportion of omega-3 fatty acid (e.g., C22:6 (n-3) DHA) and saturated fatty acids (e.g., C16:0 palmitic acid and C14:0 myristic acid). To achieve a flowable oil, the provided methods force cells to convert the saturated fatty acid to monounsaturated fatty acids including omega-6 fatty acid (e.g., C22:5 (n-6) DPA) and omega-7 fatty acids (e.g., C16:1 (n-7) palmitoleic acid and C18:1 (n-7) vaccenic acid). The zinc concentrations in the culture media induce a metabolic pathway that causes saturated fatty acids to become monounsaturated. The oils produced by the present methods have improved melting, cloud and pour points. For example, as described herein, the oils produced by the provided methods include a reduced pour point of as low as −9° C., a much lower pour point range than a typical lipids produced by previous fermentation process conditions, which varied between 18° C. and 21° C. Optionally, the oil flows at room temperature. Changing the zinc concentration caused changes in fatty acid composition and reduced melting point, cloud point, and pour point of the oil. Consequently, the oil exhibits significantly improved cold flow properties, e.g., the oil is flowable at room temperature.

As used herein, the term melting point refers to the temperature at which the oil becomes completely clear. As used herein, the term cloud point refers to the temperature of the oil at which the oil begins to crystalize. As used herein, the pour point is an index of the lowest temperature at which movement of the test specimen (e.g., oil) is observed under prescribed conditions of the test. These temperatures can be determined by known methods, including those established by the American Oil Chemistry Society (AOCS) and American Society of Testing and Materials (ASTM), which establishes specifications for determining the melting, cloud and pour points of fluids such as lipids and oils. For example, melting point can be determined using AOCS Official Method Cc 1-25, cloud point can be determined using AOCS Official Method Cc 6-25 and pour point can be determined using ASTM Official Method D97.

Provided is a method of producing oil with increased omega-7 fatty acids. The method comprises culturing oil-producing microorganisms in a fermentation medium with less than 0.3 mg/L zinc. The culturing produces an oil comprising fatty acids, wherein the oil comprises increased omega-7 fatty acids compared to a control oil. Optionally, the oil comprises DHA. Optionally, 35% or less of the fatty acids are saturated fatty acids. Optionally, less than 30% of the fatty acids in the oil are saturated fatty acids. Optionally, less than 25% of the fatty acids in the oil are saturated fatty acids.

Trace elements are ingredients normally supplied at very low levels but are commonly considered to be an important requirements for microbial growth. Trace elements include, but are not limited to, iron, copper, zinc and molybdate. For example, iron and zinc were determined to be particularly important to obtaining the optimum growth of thraustochytrids, and zinc concentration of 0.61 mg/L was considered optimum (Nagano et al., 2013 Journal of Bioscience and Bioengineering 116(3):337-39). Furthermore, zinc concentration in the range of 0.61 to 0.75 mg/L was used in the medium for the cultivation of *Schizochytrium* strains for producing DHA-rich algal lipids (EP Publication No. 2 960 325, e.g., page 10, lines 17-18). In contrast, as described herein, zinc is not essential for culture growth and altering zinc levels causes different oil profiles and properties. Thus, the provided methods include culturing the oil-producing microorganisms in a fermentation medium with less than 0.3 mg/L zinc. Optionally, the fermentation medium comprises less than 0.3, 0.29, 0.28, 0.27, 0.26, 0.25, 0.24, 0.23, 0.22, 0.21, 0.20, 0.19, 0.18, 0.17, 0.16, 0.15, 0.14, 0.13, 0.12, 0.11, 0.10, 0.09, 0.08, 0.07, 0.06, 0.05, 0.04, 0.03, 0.02, or 0.01 mg/L zinc. Optionally, zinc is not included in the trace elements added to fermentation medium used during culturing. However, zinc may be present at low levels, for example, about 0.1 mg/L in the water within the medium. Thus, the provided methods include culturing the oil-producing microorganisms in the absence of zinc or in the substantial absence of zinc. As used herein, the absence of zinc means zinc is not present in the trace elements added to the culture medium nor in the water in the medium. As used herein, the substantial absence of zinc means zinc is not present in the trace elements added to the culture medium but residual amounts of zinc may be present in the water in the medium, for example, a concentration about 0.1 mg/L zinc. Optionally, zinc is present in the trace elements added to the culture medium in an amount less than the amount of zinc in a control medium, e.g., typical culture medium. Normally, the trace elements include 3 mg/L of zinc sulfate heptahydrate (or other salt form), which is 0.682 mg/L actual zinc. The provided methods include adding to the culture medium less than about 0.68 mg/L zinc. Optionally, the provided methods include adding to the culture medium less than about 0.68, 0.65, 0.6, 0.55, 0.5, 0.45, 0.4, 0.35, 0.3, 0.25, 0.2, 0.15, 0.1, 0.05, or 0 mg/L zinc. Optionally, the provided methods include culturing the oil-producing microorganisms in a fermentation medium with less than 0.3 mg/L zinc including residual zinc present in the water. Optionally, the medium comprises from 0 to 0.1 mg/L zinc. Optionally, the medium comprises from 0 to 0.15 mg/L zinc.

Optionally, the medium comprises from 0 to 0.2 mg/L zinc. Optionally, the medium comprises from 0 to 0.3 mg/L zinc.

The oils produced by the provided methods have improved cold flow properties, e.g., they have improved melting, cloud, and pour point temperatures. Thus, the oils made by the provided methods can have a melting point of from 20 to 33° C. or any temperature between 20 and 33° C. inclusive. Thus, the oils can have a melting point temperature of 20, 21, 22, 23, 24, 25, 26, 27, 28, 29, 30, 31, 32, or 33° C. or any fraction thereof. Optionally, the oils made by the provided methods have a cloud point of from 5 to 20° C. or any temperature between 5 and 20° C. inclusive. Thus, the oils can have a cloud point temperature of 5, 6, 7, 8, 9, 10, 11, 12, 13, 14, 15, 16, 17, 18, 19, or 20° C. or any fraction thereof. Optionally, the oils made by the provided methods have a pour point of −10 to 15° C. or any temperature between −10 and 15° C. inclusive. Thus, the oils can have a pour point temperature of −10, −9, −8, −7, −6, −5, −4, −3, −2, −1, 0, 1, 2, 3, 4, 5, 6, 7, 8, 9, 10, 11, 12, 13, 14, or 15° C. or any fractional temperature between. Optionally, the lipids are flowable at a temperature of 19 to 22° C. (i.e., room temperature) or any temperature between 19 and 22° C.

As described herein, culturing the oil-producing microorganisms in the fermentation medium produces oils having fatty acids wherein less than 35% of the fatty acid in the oils are saturated fatty acids. Optionally, less than about 20%, 25% or 30% of the fatty acids in the oils are saturated fatty acids. For example, less than 15, 16, 17, 18, 19, 20, 21, 22, 23, 24, 25, 26, 27, 28, 29, 30, 31, 32, 33, 34 or 35% of the fatty acids in the oils are saturated fatty acids. Optionally, the saturated fatty acids comprise C16:0 (palmitic acid) and C14:0 (myristic acid). The percentage of saturated fatty acids is expressed throughout as a percentage of the total fatty acids in the oil. Optionally, 30% to 35% of the fatty acids in the oils are saturated fatty acids and the oils are flowable at a temperature between 9 and 15° C. Optionally, 25% to 30% of the fatty acids in the oils are saturated fatty acids and the oils are flowable at a temperature between −9° C. and 9° C. Optionally, less than 25% of the fatty acids in the oils are saturated fatty acids and the oils are flowable at a temperature between 0° C. and 4° C.

The provided methods produce oils having omega-7 fatty acids. The herein provided oils have higher omega-7 fatty acid percentages as compared to a control oils produced by previous fermentation methods. Terms like higher, increased, elevated, or elevation refer to increases above a control. For example, control levels of omega-7 fatty acids are levels produced under culturing conditions where the normal amount of zinc is present in the culture medium, e.g., about 0.69 mg/L zinc in the trace elements added to the culture medium. Control oils are oils produced by microorganisms using other fermentation methods and such control oils typically have less than 5% omega-7 fatty acids. As described herein, culturing the oil-producing microorganisms in the fermentation medium produces oils with from 10 to 30% omega-7 fatty acids. Thus, of the total fatty acids in the oils produced by the provided methods 10, 11, 12, 13, 14, 15, 16, 17, 18, 19, 20, 21, 22, 23, 24, 25, 26, 27, 28, 29, or 30% or more of the total fatty acids can be omega-7 fatty acids. The omega-7 fatty acids in the oils include, for example, palmitoleic acid (C16:1(n-7)), cis-vaccenic acid (C18:1(n-7)) or a combination thereof. Optionally, the oil comprises 5, 6, 7, 8, 9, 10, 11, 12, 13 or 14 to 15% vaccenic acid (C18:1 (n-7)). Optionally, the oil comprises 5, 6, 7, 8, 9, 10, 11, 12, 13 or 14 to 15% palmitoleic acid (C16:1(n-7)).

The oils produced by the provided methods can also include alpha linolenic acid, arachidonic acid, docosahexanenoic acid, docosapentaenoic acid, eicosapentaenoic acid, gamma-linolenic acid, linoleic acid, linolenic acid, or a combination thereof. Optionally, the oils comprise fatty acids selected from the group consisting of palmitic acid (C16:0), myristic acid (C14:0), palmitoleic acid (C16:1(n-7)), vaccenic acid (C18:1(n-7)), docosapentaenoic acid (C22:5(n-6)), docosahexaenoic acid (C22:6(n-3)), and combinations thereof. Optionally, the oil comprises at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% DHA. Optionally, the oil comprises at least 35% DHA. For example, the oil may comprise about 35 to 45% DHA.

Oil produced using the provided methods can be obtained from a variety of microorganisms including oil-producing algae, fungi, bacteria and protists. The microorganisms are optionally selected from the genus *Oblongichytrium, Aurantiochytrium, Thraustochytrium, Schizochytrium*, and *Ulkenia* or any mixture thereof. Optionally, the microorganism is a thraustochytrid of the order Thraustochytriales, more specifically Thraustochytriales of the genus *Thraustochytrium*. Exemplary microorganisms include Thraustochytriales as described in U.S. Pat. Nos. 5,340,594 and 5,340,742, which are incorporated herein by reference in their entireties. Optionally, the microorganisms are of the family Thraustochytriaceae. The microorganism can be a *Thraustochytrium* species, such as the *Thraustochytrium* species deposited as ATCC Accession No. PTA-6245 (i.e., ONC-T18), as described in U.S. Pat. No. 8,163,515, which is incorporated by reference herein in its entirety. The microorganisms can be ONC-T18.

Microalgae are acknowledged in the field to represent a diverse group of organisms. Microalgae can be of eukaryotic nature or of prokaryotic nature. Microalgae can be nonmotile or motile. The term thraustochytrid, as used herein, refers to any member of the order Thraustochytriales, which includes the family Thraustochytriaceae. Strains described as thraustochytrids include the following organisms: Order: Thraustochytriales; Family: Thraustochytriaceae; Genera: *Thraustochytrium* (Species: sp., *arudimentale, aureum, benthicola, globosum, kinnei, motivum, multirudimentale, pachydermum, proliferum, roseum, striatum*), *Ulkenia* (Species: sp., *amoeboidea, kerguelensis, minuta, profunda, radiata, sailens, sarkariana, schizochytrops, visurgensis, yorkensis*), *Schizochytrium* (Species: sp., *aggregatum, limnaceum, mangrovei, minutum, octosporuni*), Japoniochytrium (Species: sp., *marinum*), *Aplanochytrium* (Species: sp., *haliotidis, kerguelensis, profunda, stocchinoi*), *Althornia* (Species: sp., *crouchii*), or *Elina* (Species: sp., *marisalba, sinorifica*). Species described within *Ulkenia* are considered to be members of the genus *Thraustochytrium*. Strains described as being within the genus *Thraustochytrium* may share traits in common with and also be described as falling within the genus *Schizochytrium*. For example, in some taxonomic classifications ONC-T18 may be considered within the genus *Thraustochytrium*, while in other classifications it may be described as within the genus *Schizochytrium* because it comprises traits indicative of both genera.

As described, the microorganisms provided herein are cultivated under conditions that produce a compound of interest, e.g., fatty acids, or a compound of interest at a desired level (e.g., 35% or less saturated fatty acids). The culturing can be carried out for one to several days. Optionally, the method further includes extracting the oils from the microorganisms. The provided methods include or can be used in conjunction with additional steps for culturing microorganisms according to methods known in the art, obtaining the oils therefrom, or further refinind the oil. For example, a Thraustochytrid, e.g., a *Thraustochytrium*, can be cultivated and extracted according to methods described in U.S. Patent Publications 2009/0117194, 2012/0244584, or 2015/0176042, which are herein incorporated by reference in their entireties for each step of the methods or each composition included therein.

Optionally, the method includes culturing oil-producing microorganisms in fermentation medium under a controlled carbon consumption rate. Optionally, the carbon consumption rate is controlled to be between 1.0 and 4.5 g/L per hour or any range within 1.0 and 4.5 g/L per hour, e.g., 1.0 and 2.0, 1.0 and 3.0, or 1.0 and 4.0 g/L-h. Optionally, the carbon consumption rate is controlled to be between 0.01 to 0.15 g of carbon per g of biomass per hour. The carbon consumption rate can be controlled by a variety of methods. Optionally, the carbon consumption rate is controlled by aeration, agitation, vessel backpressure or a combination thereof. Optionally, the carbon consumption rate is controlled by continuous addition of a (one or more) carbon source(s) throughout the culturing.

To isolate oils from microorganisms, the microorganisms are grown in a growth medium (also known as culture medium). Any of a variety of media are suitable for use in culturing the microorganisms described herein. Optionally, the medium supplies various nutritional components, including a carbon source and a nitrogen source, for the microorganism. Medium for Thraustochytrid culture can include any of a variety of carbon sources. Examples of carbon sources include fatty acids (e.g., oleic acid), lipids, glycerols, triglycerols, carbohydrates, polyols, amino sugars, and any kind of biomass or waste stream. Carbohydrates include, but are not limited to, glucose, cellulose, hemicellulose, fructose, dextrose, xylose, lactulose, galactose, maltotriose, maltose, lactose, glycogen, gelatin, starch (corn or wheat), acetate, m-inositol (e.g., derived from corn steep liquor), galacturonic acid (e.g., derived from pectin), L-fucose (e.g., derived from galactose), gentiobiose, glucosamine, alpha-D-glucose-1-phosphate (e.g., derived from glucose), cellobiose, dextrin, alpha-cyclodextrin (e.g., derived from starch), and sucrose (e.g., from molasses). Polyols include, but are not limited to, maltitol, erythritol, and adonitol. Amino sugars include, but are not limited to, N-acetyl-D-galactosamine, N-acetyl-D-glucosamine, and N-acetyl-beta-D-mannosamine.

The microorganisms can be cultured in saline or salt-containing medium. The selected culture medium optionally includes NaCl or natural or artificial sea salt and/or artificial seawater. Thraustochytrids can be cultured, for example, in medium having a salt concentration from about 0.5 g/L to about 50.0 g/L, from about 0.5 g/L to about 35 g/L, or from about 18 g/L to about 35 g/L. Optionally, the Thraustochytrids described herein can be grown in low salt conditions (e.g., salt concentrations from about 0.5 g/L to about 20 g/L or from about 0.5 g/L to about 15 g/L).

Alternatively, the culture medium can include non-chloride-containing sodium salts as a source of sodium, with or without NaCl. Examples of non-chloride sodium salts suitable for use in accordance with the present methods include, but are not limited to, soda ash (a mixture of sodium carbonate and sodium oxide), sodium carbonate, sodium bicarbonate, sodium sulfate, and mixtures thereof. See, e.g., U.S. Pat. Nos. 5,340,742 and 6,607,900, the entire contents of each of which are incorporated by reference herein. A significant portion of the total sodium, for example, can be supplied by non-chloride salts such that less than about 100%, 75%, 50%, or 25% of the total sodium in culture medium is sodium chloride.

Media for microbial cultures can include any of a variety of nitrogen sources. Exemplary nitrogen sources include ammonium solutions (e.g., $NH_4$ in $H_2O$), ammonium or amine salts (e.g., $(NH_4)_2SO_4$, $(NH_4)_3PO_4$, $NH_4NO_3$, $NH_4OOCH_2CH_3$ ($NH_4Ac$)), peptone, tryptone, yeast extract, malt extract, fish meal, sodium glutamate, soy extract, casamino acids and distiller grains. Concentrations of nitrogen sources in suitable medium typically range between and including about 1 g/L and about 25 g/L.

The medium optionally includes a phosphate, such as potassium phosphate or sodium-phosphate. Inorganic salts and trace nutrients in medium can include ammonium sulfate, sodium bicarbonate, sodium orthovanadate, potassium chromate, sodium molybdate, selenous acid, nickel sulfate, copper sulfate, zinc sulfate, cobalt chloride, iron chloride, manganese chloride calcium chloride, and EDTA. Vitamins such as pyridoxine hydrochloride, thiamine hydrochloride, calcium pantothenate, p-aminobenzoic acid, riboflavin, nicotinic acid, biotin, folic acid and vitamin B12 can be included.

The pH of the medium can be adjusted to between and including 3.0 and 10.0 using acid or base, where appropriate, and/or using the nitrogen source. Optionally, the medium can be sterilized.

Generally a medium used for culture of a microorganism is a liquid medium. However, the medium used for culture of a microorganism can be a solid medium. In addition to carbon and nitrogen sources as discussed herein, a solid medium can contain one or more components (e.g., agar or agarose) that provide structural support and/or allow the medium to be in solid form.

The resulting biomass can be pasteurized to inactivate undesirable substances present in the biomass. For example, the biomass can be pasteurized to inactivate compound degrading substances, such as degradative enzymes. The biomass can be present in the fermentation medium or isolated from the fermentation medium for the pasteurization step. The pasteurization step can be performed by heating the biomass and/or fermentation medium to an elevated temperature. For example, the biomass and/or fermentation medium can be heated to a temperature from about 50° C. to about 95° C. (e.g., from about 55° C. to about 90° C. or from about 65° C. to about 80° C.). Optionally, the biomass and/or fermentation medium can be heated from about 30 minutes to about 120 minutes (e.g., from about 45 minutes to about 90 minutes, or from about 55 minutes to about 75 minutes). The pasteurization can be performed using a suitable heating means, such as, for example, by direct steam injection.

The biomass can be harvested according to a variety of methods, including those currently known to one skilled in the art. For example, the biomass can be collected from the fermentation medium using, for example, centrifugation (e.g., with a solid-ejecting centrifuge) and/or filtration (e.g., cross-flow filtration). Optionally, the harvesting step includes use of a precipitation agent for the accelerated collection of cellular biomass (e.g., sodium phosphate or calcium chloride).

The biomass is optionally washed with water. The biomass can be concentrated up to about 20% solids. For example, the biomass can be concentrated from about 1% to about 20% solids, from about 5% to about 20%, from about 7.5% to about 15% solids, or to any percentage within the recited ranges.

Optionally, the oils can be further processed, e.g., by winterization. Prior to winterization, the oils or polyunsaturated fatty acids are obtained or extracted from the biomass or microorganisms using one or more of a variety of methods, including those currently known to one of skill in the art. For example, methods of isolating oils or polyunsaturated fatty acids are described in U.S. Pat. No. 8,163,515, which is incorporated by reference herein in its entirety. Alternatively, the oils or polyunsaturated fatty acids are isolated as described in U.S. Publication No. 2015/0176042, which is incorporated by reference herein in its entirety. Optionally, the one or more polyunsaturated fatty acids are selected from the group consisting of alpha linolenic acid, arachidonic acid, docosahexanenoic acid, docosapentaenoic acid, eicosapentaenoic acid, gamma-linolenic acid, linoleic acid, linolenic acid, and combinations thereof.

Oils, lipids or derivatives thereof (e.g., polyunsaturated fatty acids (PUFAs) and other lipids) can be utilized in any of a variety of applications exploiting their biological, nutritional, or chemical properties. Thus, the oils, lipids or derivatives thereof can be used to produce biofuel. Optionally, the oils, lipids or derivatives thereof, are used in pharmaceuticals, nutraceuticals, food supplements, animal feed additives, cosmetics, and the like.

Optionally, the oils or biomass produced according to the methods described herein can be incorporated into a final product (e.g., a food or feed supplement, an infant formula, a pharmaceutical, a fuel, and the like). Optionally, the biomass can be incorporated into animal feed, for example, feed for cows, horses, fish or other animals. Optionally, the oils can be incorporated into nutritional or dietary supplements like vitamins. Suitable food or feed supplements into which the oils or lipids can be incorporated include beverages such as milk, water, sports drinks, energy drinks, teas, and juices; confections such as candies, jellies, and biscuits; fat-containing foods and beverages such as dairy products; processed food products such as soft rice (or porridge); infant formulae; breakfast cereals; or the like.

Optionally, one or more of the oils or compounds therein (e.g., PUFAs) can be incorporated into a nutraceutical or pharmaceutical product. Examples of such nutraceuticals or pharmaceuticals include various types of tablets, capsules, drinkable agents, etc. Optionally, the nutraceutical or pharmaceutical is suitable for topical application or oral applications. Dosage forms can include, for example, capsules, oils, granula, granula subtilae, pulveres, tabellae, pilulae, trochisci, or the like.

The oils or oil portions thereof produced according to the methods described herein can be incorporated into products in combination with any of a variety of other agents. For instance, the oils or biomass can be combined with one or more binders or fillers, chelating agents, pigments, salts, surfactants, moisturizers, viscosity modifiers, thickeners, emollients, fragrances, preservatives, etc., or any combination thereof.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

The examples below are intended to further illustrate certain aspects of the methods and compositions described herein, and are not intended to limit the scope of the claims.

EXAMPLES

A thraustochytrid strain deposited as ATCC Accession No. PTA-6245, also known as T18, was used in all examples. This strain produces lipids that contains several major fatty acids, including C14:0 myristic acid, C16:0 palmitic acid, C16:1 (n-7) palmitoleic acid, C18:1 (n-9) vaccenic acid, C22:5 (n-6) docosapentaenoic acid (DPA) and C22:6 (n-3) docosahexaenoic acid (DHA). As described herein, depending on fermentation conditions applied, the level of synthesis of each major fatty acids may be altered, and consequently the relative content of these major fatty acids within the entire lipid profile can be varied. The different process conditions lead lipid synthesis toward more desirable fatty acid profiles, namely higher DHA and higher monounsaturated fatty acids (MUFA) and reduced saturated fatty acids (SFA) as compared to levels in the absence of the condition.

Example 1. Reduction of Trace Elements

This example illustrates typical fatty acid profiles attainable by microbial fermentations with controlled carbon consumption rate. Fermentation was carried out in a 30 L fermentor with a working volume between 20 L and 30 L, with the increase in volume due to the feeding of glucose syrup during the fermentation. Control fermentation medium with the normal amount of zinc contained (per liter): glucose 60 g, soy peptone 2 g; sodium chloride 1.65 g; magnesium sulfate heptahydrate 4 g; potassium phosphate monobasic 2.2 g; potassium phosphate dibasic 2.4 g; ammonium sulfate 20 g; calcium chloride dihydrate 0.1 g; iron chloride 3 mg; copper sulfate pentahydrate 3 mg; sodium molybdate dehydrate 1.5 mg; zinc sulfate heptahydrate 3 mg; cobalt chloride hexahydrate 1.5 mg; manganese chloride tetrahydrate 1.5 mg; nickel sulfate hexahydrate 1.5 mg; vitamin B12 0.03 mg; biotin 0.03 mg; and thiamin hydrochloride 6 mg. A silicon based antifoam was used sparingly to suppress foam formation when necessary, and less than 0.3 g/L of this antifoam was used throughout the entire fermentation. Agitation and aeration of the fermentor were controlled such that the culture had unrestricted carbon consumption rate that was up to 3 g/L-h. Additional carbon in the form of glucose syrup was fed to the fermentor throughout the culturing or fermentation such that there was always glucose available in the media for the culture to consume.

Figure 2:
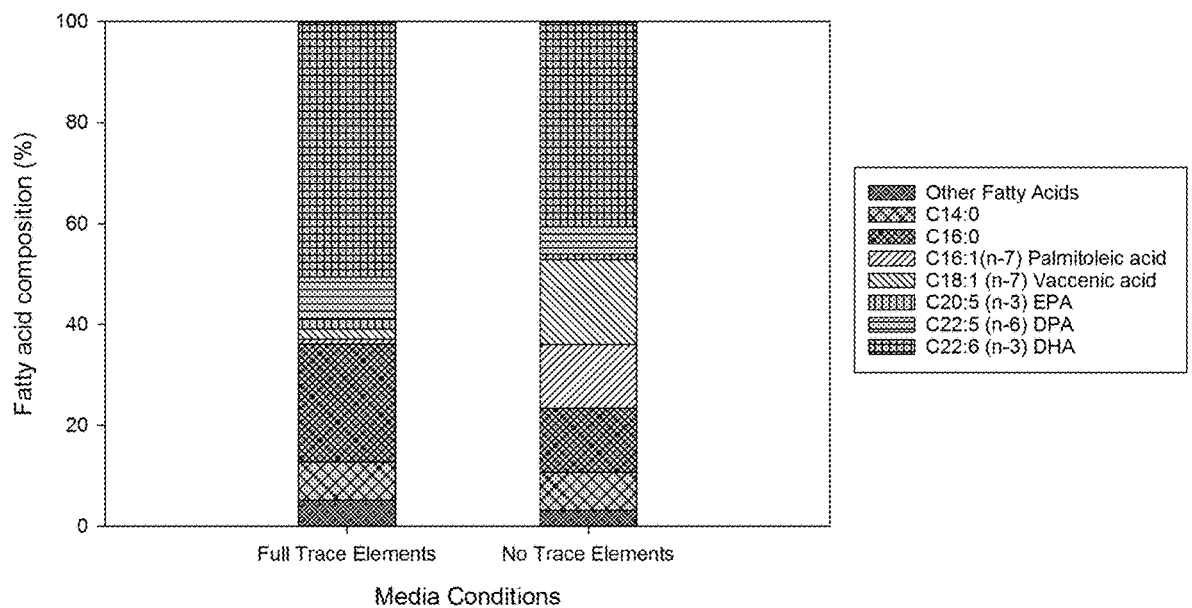
FIG. 2 is a graph showing the final fatty acid profile of total lipid produced by thraustochytrid culture with and without trace element addition. The profile of the control culture was roughly composed of saturated fatty acids (C14:0, C16:0), monounsaturated fatty acids (C16:1(n-7) palmitoleic acid and 18:1 (n-7) vaccenic acid) and polyunsaturated fatty acids (C20:5 (n-3) eicosapentaenoic acid (EPA), C22:5 (n-6) docosapentaenoic acid (DPA) and C22:6(n-3) DHA). When trace elements copper, molybdate and zinc are not added to the culture medium, monounsaturated fatty acids make up more of the oil profile.
Figure 3:
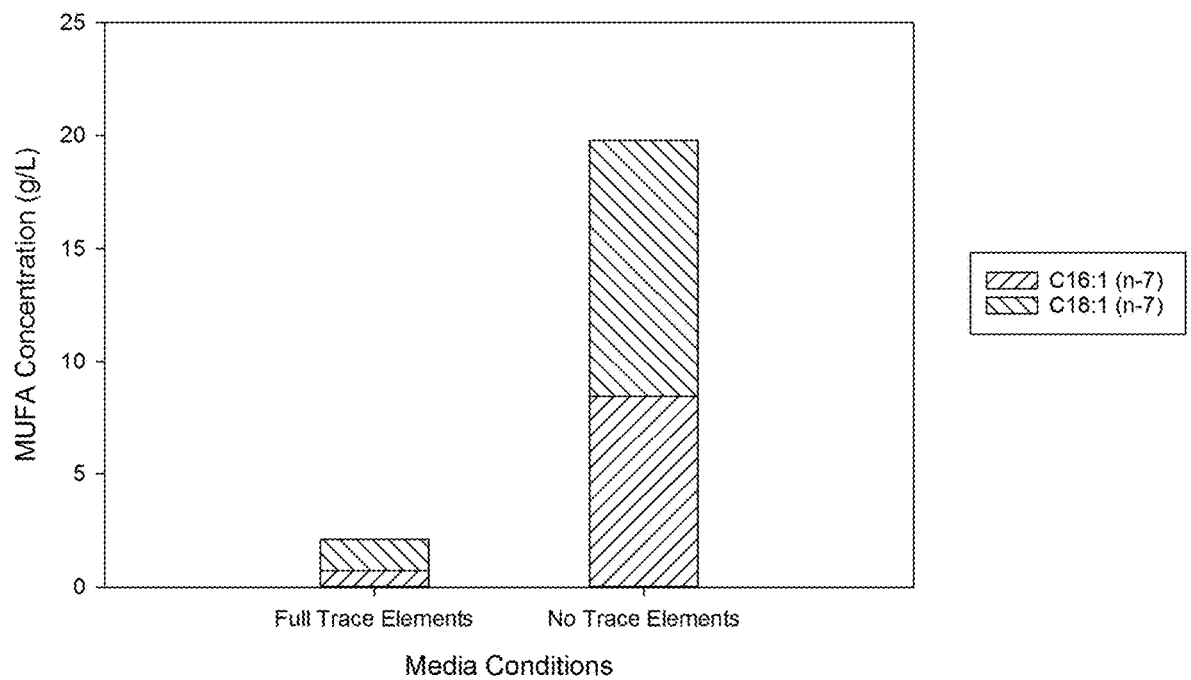
FIG. 3 is a graph showing production titer in g/L of monounsaturated fatty acids in cultures grown with and without trace element addition. C16:1(n-7) palmitoleic acid and 18:1 (n-7) vaccenic acid are the predominant members of the monounsaturated fatty acids in the organism's lipid profile.

In an attempt to reduce media cost, three of the ingredients were removed from the culture media. Previous small scale experiments showed copper sulfate pentahydrate, sodium molybdate dehydrate and zinc sulfate heptahydrate might not be essential for culture growth. These ingredients are referred to as trace elements because they are supplied normally at very low levels and are generally considered to be an important supply of elements required for culture growth. Fermentations were conducted to investigate how oil profiles and productivity were impacted in the absence of trace elements to the culture medium. A control fermentation, referred to in Table 1 and the figures as "Full Trace Elements," was provided with a full complement of trace elements added thereto including about 0.68 mg/L zinc. The water contained about 0.1 mg/L zinc. Therefore, the control fermentation medium includes about 0.8 mg/L zinc. There was no copper sulfate pentahydrate, sodium molybdate dehydrate and zinc sulfate heptahydrate supplied to the test fermentation medium, which is referred to in Table 1 and the figures as "No Trace Elements." However, the water still contained about 0.1 mg/L zinc. Surprisingly, MUFA levels increased sharply in cultures that lacked copper, molybdate and zinc in the test fermentation medium. Specifically, palmitoleic acid content of the total fatty acids increased from 1.03% to 12.58% and vaccenic acid content of the total fatty acids increased from 1.94% to 16.87% (Table 1), increasing the overall MUFA content of the total fatty acids from 2.97% (control medium) to 29.45% (test medium) (FIG. 1). Palmitic acid decreased from 23.26% to 12.59% and DHA decreased from 50.65% to 4.56% in the test medium as shown in Table 1. However, a DHA content of 40% is still sufficient. The values in Table 1 are the percent of the fatty acids in the total fatty acids of the oil. FIG. 2 shows, in the control medium, the profile is roughly composed of saturated fatty acids (C14:0, C16:0), monounsaturated fatty acids (C16:1(n-7) palmitoleic acid and 18:1 (n-7) vaccenic acid) and polyunsaturated fatty acids (C20:5 (n-3) EPA, C22:5 (n-6) DPA and C22:6(n-3) DHA). When the test fermentation medium was used, monounsaturated fatty acids made up more of the oil profile (FIG. 2). C16:1(n-7) palmitoleic acid and 18:1 (n-7) vaccenic acid were the predominant members of the monounsaturated fatty acids in cultures grown in the test fermentation medium (FIG. 3).

Example 2. Zinc is Responsible for MUFA Suppression

Figure 4:
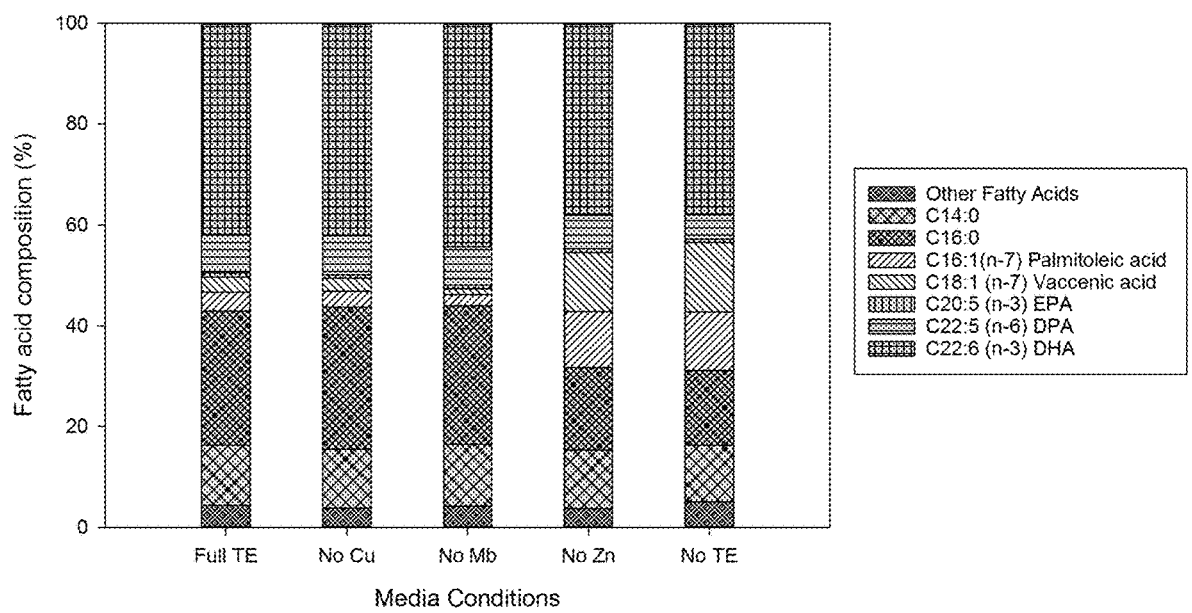
FIG. 4 is a graph showing the final fatty acid profile of total lipid produced by thraustochytrid culture with and without individual trace elements added to the culture medium. The lipid profile of the control was roughly composed of saturated fatty acids (C14:0, C16:0), monounsaturated fatty acids (C16:1(n-7) palmitoleic acid and 18:1 (n-7) vaccenic acid) and polyunsaturated fatty acids (C20:5 (n-3) EPA, C22:5 (n-6) DPA and C22:6(n-3) DHA). When zinc is not added to the culture medium, monounsaturated fatty acids make up a larger portion of the total lipid profile. Copper and molybdate removal does not produce an altered lipid profile compared to the culture provided with a full complement of trace elements.
Figure 5:
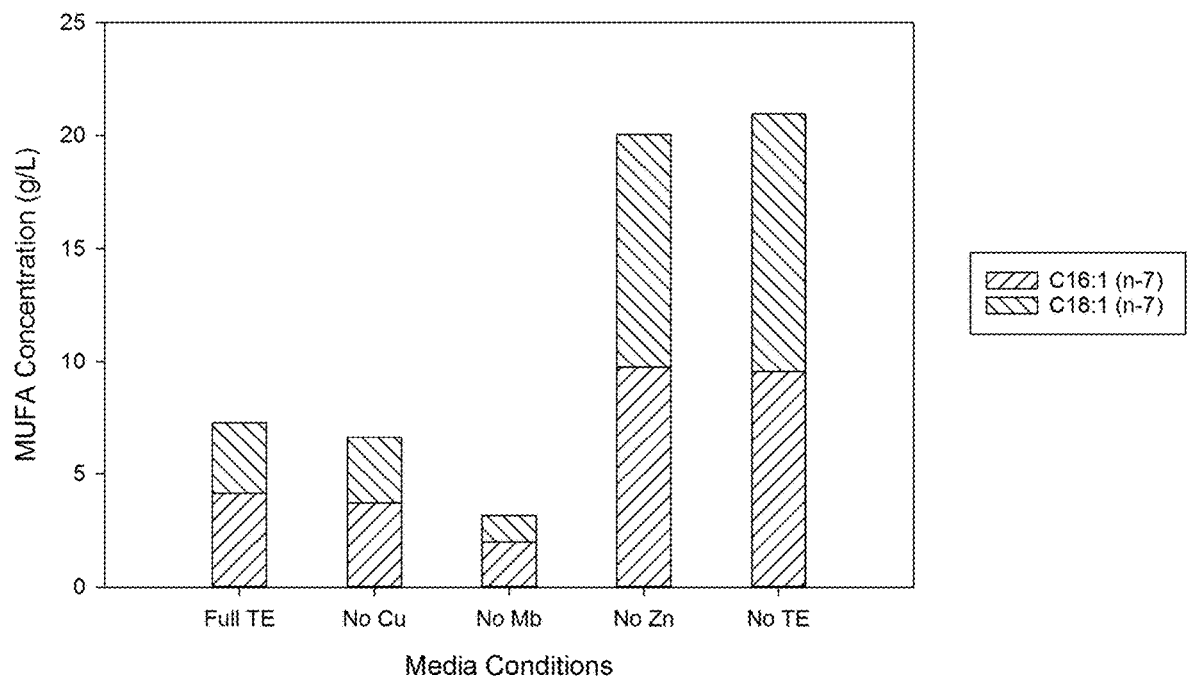
FIG. 5 is a graph showing production titer in g/L of monounsaturated fatty acids in cultures grown with and without addition of trace elements (TE): copper (Cu); zinc (Zn); and molybdate (Mb). C16:1(n-7) palmitoleic acid and 18:1 (n-7) vaccenic acid are the predominant members of the monounsaturated fatty acids in the organism's lipid profile.

This example illustrates zinc is the trace element responsible for the suppression of MUFA synthesis. Fermentations were carried out in 7 L fermentors. Control fermentation medium contained the same nutrient formulation as example 1. A fermentation medium lacking copper sulfate pentahydrate, sodium molybdate dehydrate and zinc sulfate heptahydrate was prepared and is referred to as "No TE" in FIGS. 4 and 5 and Table 2. Three additional fermentation media were prepared. One lacked copper ("No Cu"), another lacked molybdate ("No Mb") and the third lacked zinc ("No Zn"). However, the "No Zn" medium still included residual zinc from the water at about 0.1 mg/L. These media were prepared to identify which of the three triggered MUFA production when removed. Experiments were run in duplicate and averages are presented. The oil profile of cultures that were not exposed to zinc ("No Zn") was very similar to that of a culture that had no trace elements added ("No TE") (Table 2). MUFA content in cultures lacking trace elements and zinc were 25.31% and 22.85% respectively while MUFA content in cultures that lacked copper (5.76%) or molybdenum (3.36%) were very similar to cultures that contained a full complement of trace elements (6.73%). The two main saturated fatty acids in the lipid profiles were myristic acid (C14:0) and palmitic acid (C16:0). Other saturated fatty acids were present in the lipid profile (C12:0, C13:0, C15:0, C17:0, C18:0 and C20:0) in much lower concentrations and are accounted for in the data under the "other fatty acids" category. Myristic acid concentration remained unchanged (11.21-12.22%) no matter which fermentation media was used. Cultures lacking zinc ("No Zn" and "No TE") saw a large reduction in palmitic acid, (14.9 and 16.37%, Table 2), compared to the cultures that contained added zinc (28.21 ("No Cu"), 27.62 ("No Mb") and 26.69% ("Full TE"), Table 2). Consequently, the saturated fatty acid content in cultures lacking zinc was much lower (31.21% ("No TE") and 31.72% ("No Zn"), Table 2) than that of cultures with zinc. Such an oil profile has improved cold flow properties. Cultures that grew without copper and molybdate produced lipid profiles with 43.72% and 44.05% saturated fatty acids respectively, which is very similar to the control culture lipid which contained 42.97% saturates. None of these three cultures produced an oil with improved cold flow properties, e.g., an oil flowable at room temperature. Copper and molybdate removal does not produce an altered lipid profile compared to the culture provided with a full complement of trace elements (FIG. 4). C16:1(n-7) Palmitoleic acid and 18:1 (n-7) vaccenic acid are the predominant members of the monounsaturated fatty acids in cultures grown without added zinc (FIG. 5, "No Zn" and "No TE"), and the total quantity of omega-7 fatty acids was increased by 175%, from 7.27 g/L to 20.03 g/L (FIG. 5, "No Zn" and "Full TE").

TABLE 1

Fatty acid profile of cultures grown with and without addition of trace elements

| Major fatty acids (values are percentage of total fatty acids) | Full Trace Elements | No Trace Elements |
| --- | --- | --- |
| Other fatty acids | 5.15 | 3.20 |
| C14:0 Myristic acid | 7.63 | 7.56 |
| C16:0 Palmitic acid | 23.26 | 12.59 |
| C16:1 (n-7) Palmitoleic acid | 1.03 | 12.58 |
| C18:1 (n-7) Vaccenic acid | 1.94 | 16.87 |
| C20:5 (n-3) EPA | 1.95 | 1.05 |
| C22:5 (n-6) DPA | 8.39 | 5.59 |
| C22:6 (n-3) DHA | 50.65 | 40.56 |

TABLE 2

Fatty acid profile of cultures grown without individual trace elements

| Major fatty acids (% of total fatty acids) | Full TE | No Cu | No Mb | No Zn | No TE |
| --- | --- | --- | --- | --- | --- |
| Other fatty acids | 4.48 | 3.85 | 4.21 | 3.8 | 5.10 |
| C14:0 Myristic acid | 11.80 | 11.66 | 12.22 | 11.55 | 11.21 |
| C16:0 Palmitic acid | 26.69 | 28.21 | 27.62 | 16.37 | 14.90 |

TABLE 2-continued

Fatty acid profile of cultures grown
without individual trace elements

| Major fatty acids (% of total fatty acids) | Full TE | No Cu | No Mb | No Zn | No TE |
|---|---|---|---|---|---|
| C16:1 (n-7) Palmitoleic acid | 3.78 | 3.22 | 2.13 | 11.09 | 11.53 |
| C18:1 (n-7) Vaccenic acid | 2.95 | 2.54 | 1.23 | 11.76 | 13.78 |
| C20:5 (n-3) EPA | 0.84 | 0.68 | 0.77 | 0.74 | 0.76 |
| C22:5 (n-6) DPA | 7.62 | 7.70 | 7.53 | 6.57 | 4.72 |
| C22:6 (n-3) DHA | 41.84 | 42.14 | 44.29 | 38.12 | 38.00 |

Figure 6:
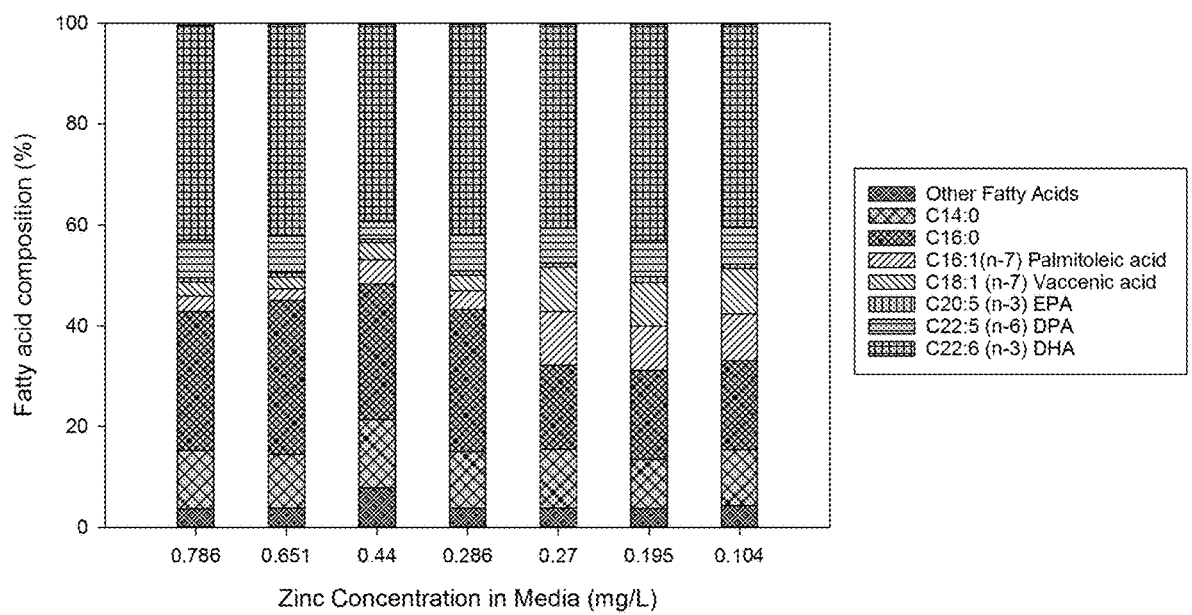
FIG. 6 is a graph showing the final fatty acid profile of total lipid produced by a thraustochytrid culture with varying concentrations of the trace element zinc added to the culture medium. Zinc was added to the media in the form of zinc sulfate heptahydrate such that the initial concentration of elemental zinc equaled about 0.78, 0.65, 0.44, 0.29, 0.27, 0.2 and 0.10 mg/L respectively. The lipid profile of the control oil was roughly composed of saturated fatty acids (C14:0, C16:0), monounsaturated fatty acids (C16:1(n-7) palmitoleic acid and 18:1 (n-7) vaccenic acid) and polyunsaturated fatty acids (C20:5 (n-3) EPA, C22:5 (n-6) DPA and C22:6(n-3) DHA). When reduced amounts of zinc were added to the culture medium, monounsaturated fatty acids make up a larger portion of the total lipid profile.
Figure 7:
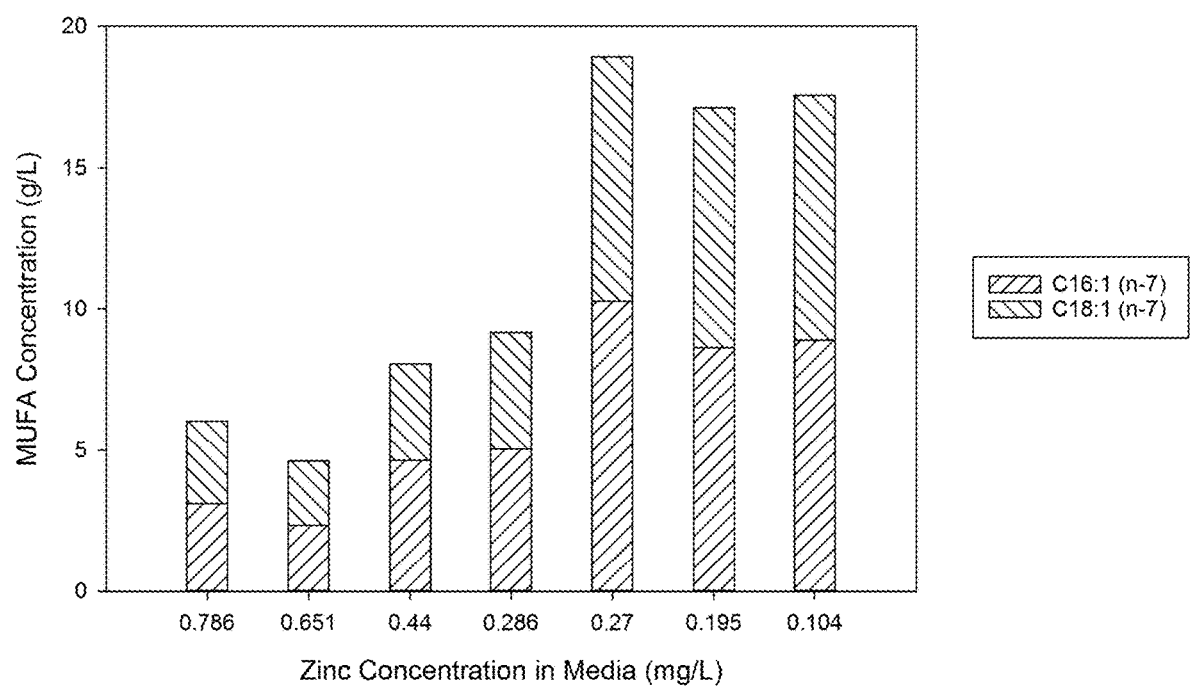
FIG. 7 is a graph showing production titer in g/L of monounsaturated fatty acids in cultures grown with different concentrations of elemental zinc in the form of zinc sulfate heptahydrate. C16:1(n-7) palmitoleic acid and 18:1 (n-7) vaccenic acid are the predominant members of the monounsaturated fatty acids in the organism's lipid profile.

Further experiments were conducted to identify the maximum concentration of zinc in culture media that would result in an increased MUFA content. As noted above, analysis of municipal water supply indicated that zinc content in local water was about 0.1 mg/L. Elemental zinc is added to the media in the form of zinc sulfate heptahydrate to an initial concentration of 0.682 mg/L. Consequently the full trace elements control fermentation medium contained 0.786 mg/L zinc or about 0.8 mg/L. Media with no additional zinc added contained about 0.1 mg/L zinc. Several concentrations of added zinc were tested between these two points (Table 3). As added zinc concentration is lowered, MUFA content remains stable at below 10% until a concentration of zinc about 0.270 mg/L. At concentrations below about 0.3 mg/L MUFA content is consistently above 10%. FIG. 6 shows when the amount of zinc added to the culture medium is reduced, monounsaturated fatty acids make up a larger portion of the total lipid profile. Further, C16:1(n-7) palmitoleic acid and 18:1 (n-7) vaccenic acid are the predominant members of the monounsaturated fatty acids (FIG. 7).

TABLE 3

Fatty acid profile of cultures grown
with varying concentrations of zinc

| Major fatty acids (values are % of total fatty acids) | Elemental zinc in media (mg/L) | | | | | | |
|---|---|---|---|---|---|---|---|
| | 0.786 | 0.651 | 0.440 | 0.286 | 0.270 | 0.195 | 0.104 |
| Other fatty acids | 3.67 | 3.86 | 7.86 | 3.84 | 3.88 | 3.78 | 4.31 |
| C14:0 Myristic acid | 11.60 | 10.65 | 13.50 | 11.19 | 11.58 | 9.78 | 11.09 |
| C16:0 Palmitic acid | 27.57 | 30.57 | 27.01 | 28.23 | 16.81 | 17.61 | 17.66 |
| C16:1 (n-7) Palmitoleic acid | 3.05 | 2.33 | 4.72 | 3.71 | 10.54 | 8.81 | 9.29 |
| C18:1 (n-7) Vaccenic acid | 2.86 | 2.26 | 3.48 | 3.09 | 8.85 | 8.64 | 9.05 |
| C20:5 (n-3) EPA | 0.81 | 0.83 | 0.67 | 0.91 | 0.80 | 1.10 | 0.88 |
| C22:5 (n-6) DPA | 7.46 | 7.34 | 3.45 | 7.25 | 6.89 | 7.20 | 7.35 |
| C22:6 (n-3) DHA | 42.68 | 42.16 | 39.31 | 41.78 | 40.65 | 43.08 | 40.37 |

Example 3. MUFA Production Throughout the Fermentation

Figure 8:
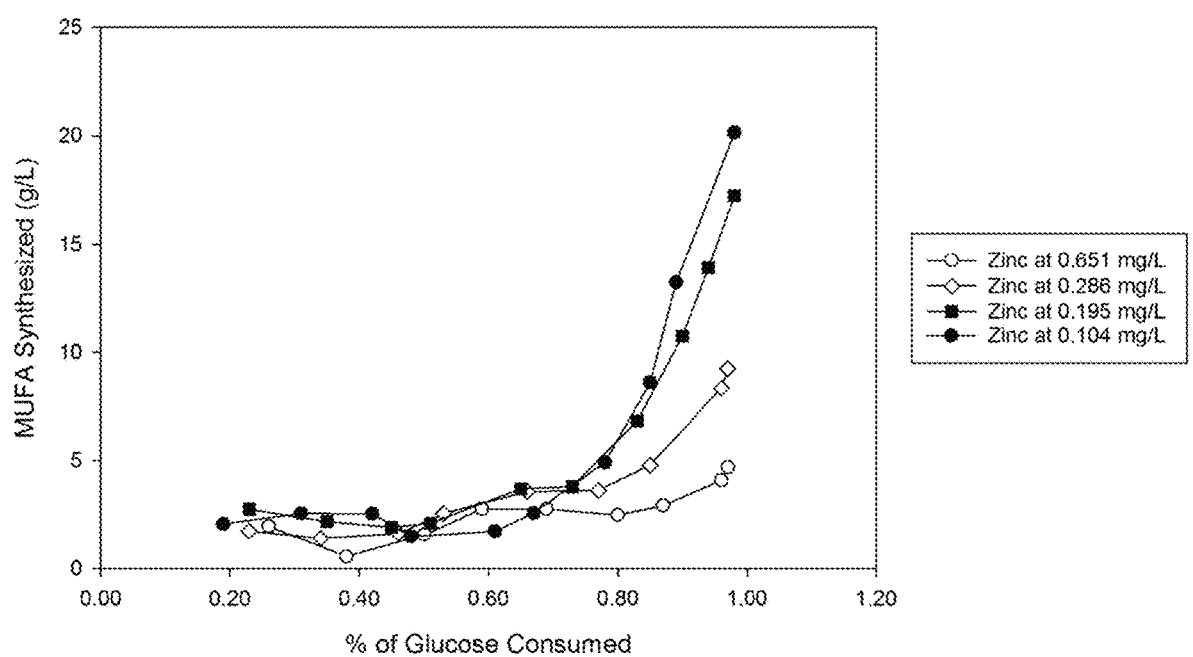
FIG. 8 is a graph showing production titer in g/L of monounsaturated fatty acids in cultures grown with concentrations of 0.65 mg/L, 0.29 mg/L, 0.2 mg/L and 0.104 mg/L of elemental zinc. MUFA production is plotted against carbon consumed (%). C16:1(n-7) palmitoleic acid and 18:1 (n-7) vaccenic acid are the predominant members of the monounsaturated fatty acids in this organism's lipid.

MUFA production in zinc-restricted cultures happens in a time dependent manner. Thraustochytrids were cultured in a fed-batch fermentation and approximately 440 g/L glucose was consumed over the course of the fermentation. Consumption rates were maintained between 2 and 3 g/L-h. Due to differences in fermentation control, the process described in this and previous examples can take between 100-300 hours. Consequently, the fermentations discussed in this Example were standardized to a percent of total carbon consumed rather than time. Cultures were provided with 0.104, 0.195, 0.286 and 0.651 mg/L of elemental zinc. The 0.104 mg/L zinc is the amount of zinc present in the water and no additional zinc was added to this culture medium. After 80% of the available carbon is consumed cultures with concentrations of zinc less than 0.65 mg/L start to produce MUFA while cultures with excess zinc show no increase in the overall MUFA content. (Table 4) During the final hours of the fermentation process, roughly 23 g/L of biomass was produced in all fermentations and between 80 and 100% of that new biomass was lipid. Table 4 shows the change in fatty acid profile during consumption of the final 20% of the carbon feed. In cultures that were provided a concentration of zinc less than 0.65 mg/L, the majority of the new lipids produced were in the form of palmitoleic (C16:1 (n-7)), vaccenic (C18:1 (n-7)) and docosahexanoic acids (C22:6 (n-3)) (Table 4 and FIG. 8). While the control culture containing 0.65 mg/L added zinc, which was provided with full trace elements, mostly produced new palmitic acid (C16:0) and docosahexaenoic acids. In cultures with less than 0.65 mg/L added zinc, monounsaturated fatty acids made up 32%, 60% and 56% of all new lipids produced while only 11% of all new lipids produced by the control culture was MUFA.

TABLE 4

Change in fatty acid quantity during consumption
of final 20% of carbon feed

| Major fatty acids (g/L) | 0.651 mg/L (control Zn) | 0.286 mg/L Zn | 0.195 mg/L Zn | 0.104 mg/L Zn |
|---|---|---|---|---|
| C14:0 Myristic acid | 1.26 | 1.03 | 0.84 | 2.8 |
| C16:0 Palmitic acid | 4.62 | 0.69 | −3.38 | −1.45 |
| C16:1 (n-7) Palmitoleic acid | 0.91 | 3.01 | 5.23 | 7.76 |
| C18:1 (n-7) Vaccenic acid | 1.29 | 2.61 | 5.20 | 7.48 |

The increase in MUFA content in the lipid profile came at the expense of saturated fatty acids. Here we have described a method to reduce saturated fatty acid production and promote MUFA production by changing the amount of zinc added to culture media. Low zinc in the medium results in an oil with improved cold flow properties and low saturated fatty acid content. This process does not reduce biomass content or total lipid content of the culture and improves the value of microbial oil without increasing cost, processing, or addition of a processing aid.

What is claimed is:

1. A method of producing oil with increased omega-7 fatty acids comprising culturing oil-producing *Thraustochytrium* microorganisms in a fermentation medium with less than 0.3 mg/L zinc, wherein the culturing produces an oil comprising fatty acids, wherein the oil comprises docosahexaenoic acid (DHA), wherein the oil comprises less than 20% palmitic acid (C16:0) and increased omega-7 fatty acids compared to a control oil.

2. The method of claim 1, wherein the oil comprising fatty acids comprises saturated fatty acids comprising C16:0 (palmitic acid) and C14:0 (myristic acid).

3. The method of claim 1, wherein the control oil comprises less than 5% omega-7 fatty acids.

4. The method of claim 1, wherein the oil comprises 10 to 30% omega-7 fatty acids.

5. The method of claim 1, wherein the omega-7 fatty acids comprise palmitoleic acid (C16:1(n-7)), vaccenic acid (C18:1(n-7)) or a combination thereof.

6. The method of claim 1, wherein the oil comprises 5 to 15% vaccenic acid (C18:1 (n-7)).

7. The method of claim 1, wherein the oil comprises 5 to 15% palmitoleic acid (C16:1(n-7)).

8. The method of claim 1, wherein culturing is carried out for one to several days.

9. The method of claim 1, wherein the microorganisms have ATCC accession number PTA-6245.

10. The method of claim 1, further comprising extracting the oil from the microorganisms.

11. The method of claim 1, wherein the medium comprises from 0 to 0.1 mg/L zinc.

12. The method of claim 1, wherein the medium comprises from 0 to 0.15 mg/L zinc.

13. The method of claim 1, wherein the medium comprises from 0 to 0.2 mg/L zinc.

14. The method of claim 1, wherein the medium comprises from 0 to 2.9 mg/L zinc.

15. The method of claim 1, wherein the oil comprises at least 15% DHA.

16. The method of claim 1, wherein the oil comprises at least 35% DHA.

17. The method of claim 1, wherein the oil comprises 35 to 45% DHA.

18. The method of claim 1, wherein the controlled carbon consumption rate is between 1 and 4 g/L-h.

19. A method of producing oil with increased omega-7 fatty acids comprising culturing oil-producing *Thraustochytrium* microorganisms in a fermentation medium with less than 0.3 mg/L zinc, wherein the culturing produces an oil comprising fatty acids, wherein the oil comprises increased omega-7 fatty acids compared to a control oil, wherein the oil comprises less than 20% palmitic acid (C16:0) and wherein 35% or less of the fatty acids are saturated fatty acids.

20. The method of claim 19, wherein less than 30% of the fatty acids in the oil are saturated fatty acids.

21. The method of claim 19, wherein less than 25% of the fatty acids in the oil are saturated fatty acids.

22. The method of claim 19, wherein the oil comprising fatty acids comprises saturated fatty acids comprising C16:0 (palmitic acid) and C14:0 (myristic acid).

23. The method of claim 19, wherein the control oil comprises less than 5% omega-7 fatty acids.

24. The method of claim 19, wherein the oil comprises 10 to 30% omega-7 fatty acids.

25. The method of claim 19, wherein the omega-7 fatty acids comprise palmitoleic acid (C16:1(n-7)), vaccenic acid (C18:1(n-7)) or a combination thereof.

26. The method of claim 19, wherein the oil comprises 5 to 15% vaccenic acid (C18:1 (n-7)).

27. The method of claim 19, wherein the oil comprises 5 to 15% palmitoleic acid (C16:1(n-7)).

28. The method of claim 19, wherein culturing is carried out for one to several days.

29. The method of claim 19, wherein the microorganisms have ATCC accession number PTA-6245.

30. The method of claim 19, further comprising extracting the oil from the microorganisms.

31. The method of claim 19, wherein the medium comprises from 0 to 0.1 mg/L zinc.

32. The method of claim 19, wherein the medium comprises from 0 to 0.15 mg/L zinc.

33. The method of claim 19, wherein the medium comprises from 0 to 0.2 mg/L zinc.

34. The method of claim 19, wherein the medium comprises from 0 to 2.9 mg/L zinc.

35. The method of claim 19, wherein the oil comprises at least 15% docosahexaenoic acid (DHA).

36. The method of claim 19, wherein the oil comprises at least 35% DHA.

37. The method of claim 19, wherein the oil comprises 35 to 45% DHA.

* * * * *